United States Patent [19] [11] 4,054,588
Siclari et al. [45] Oct. 18, 1977

[54] PROCESS FOR THE PREPARATION IN A SINGLE STAGE OF SATURATED OMEGA-AMINOACIDS FROM OLEFINICALLY UNSATURATED OMEGA-ALDEHYDOACIDS

[75] Inventors: Francesco Siclari, Barlassina; Pietro Paolo Rossi, Garlasco; Mario De Gaetano, Seregno, all of Italy

[73] Assignee: Snia Viscosa-Societa' Nazionale Industria Applicazioni Viscosa S.P.A., Italy

[21] Appl. No.: 658,589

[22] Filed: Feb. 17, 1976

[30] Foreign Application Priority Data

Feb. 25, 1975 Italy .................................. 20590/75

[51] Int. Cl.$^2$ ............................ C09F 5/00; C11C 3/00
[52] U.S. Cl. .................................. 260/404; 260/534 R
[58] Field of Search .......................... 260/404, 534 R

[56] References Cited

U.S. PATENT DOCUMENTS

| 2,777,873 | 1/1957 | Hasek | 260/404 X |
| 2,871,247 | 1/1959 | Seon et al. | 260/404 |
| 3,235,576 | 2/1966 | Chiusoli et al. | 260/404 X |
| 3,883,586 | 9/1975 | Yokoyama et al. | 260/404 |

Primary Examiner—Winston A. Douglas
Assistant Examiner—John F. Niebling
Attorney, Agent, or Firm—McGlew and Tuttle

[57] ABSTRACT

The specification describes a process for preparing saturated omega-aminoacids from olefinically unsaturated omega-aldehydoacids. According to the invention, the starting aldehydoacid is transformed into the corresponding iminoacid, and this is subjected to the hydrogenation both of the imino function and of the ethylenic double bond or double bonds, in a single stage and in the presence of an hydrogenation catalyst. The catalyst is a transition metal of one of the first two sub-groups of the VIII group of the periodic system, viz. is chosen among Fe, Ru, Os, Co, Rh, and Ir, and is used in the metal state or as a compound.

20 Claims, No Drawings

PROCESS FOR THE PREPARATION IN A SINGLE STAGE OF SATURATED OMEGA-AMINOACIDS FROM OLEFINICALLY UNSATURATED OMEGA-ALDEHYDOACIDS

BACKGROUND OF THE INVENTION

1. Field of the Invention

This invention relates to a process for transforming, in a single stage, olefinically unsaturated omega-aldehydoacids into saturated omega-amino-acids. The industrial importance of these useful products is well known and requires no demonstration. It suffices to recall, for instance, the very widespread use of these aminoacids as monomers for the manufacture of polyamides employed as plastic materials or in the textile field, for the production of "nylon" fibers and yarns.

2. Description of the Prior Art

These omega-aminoacids are defined by the general formula $H_2N-(CH_2-)_{n+1}COOH$ wherein "$n$" is a whole number in the range from 4 to 16, and more commonly from 4 to 10.

The olefinically unsaturated omega-aldehydoacids have been disclosed by the publication of patent applications No. 74 24188 in France and Pat. No. P 24 33408 in the German Federal Republic by the applicant of this application. In said publications the methodology for obtaining such unsaturated aldehydoacids starting from cycloolefins comprising more than one ethylenic unsaturation, has also been described. Several omega-formyl-alkenoic acids, such as 11-formyl-4,8-undecadienoic acid, 7-formyl-4-heptenoic acid, 9-formyl-4-nonenoic acid and 9-formyl-6-nonenoic acid, with the respective production methodologies, had been described in the aforesaid publications.

In a more general form, the linear unsaturated aldehydoacids which can be used according to the present invention to obtain the desired saturated omega-aminoacids, may contain from 1 to 3 olefinic double bonds and correspond therefore to the general formula

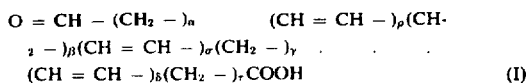

$$(CH = CH -)_\delta(CH_2 -)_\tau COOH \quad (I)$$

wherein $\alpha, \beta, \gamma, \delta$ = whole numbers, equal or different from one another, chosen among 0,1,2 and 3;

$\rho, \sigma, \tau$ = whole numbers, equal or different from one another, chosen among 0 and 1;

provided that the following conditions are observed:

the sum $\rho + \sigma + \tau = 1,2$ or 3;
the sum $\alpha + \beta + \gamma + \delta + \rho + \sigma + \tau = n$ (Examples: 7-formyl-4-heptenoic acid wherein $\alpha = 2$, $\beta = 2, \gamma = 0, \delta = 0, \rho = 1, \sigma = 0, n = 6$;
11-formyl-4,8-undecadienoic acid, wherein $\alpha = 2, \beta = 2, \gamma = 2, \delta = 0, \rho = 1, \tau = 0, n = 10$.)

In the aforesaid patent publications the use of these unsaturated omega-aldehydoacids to obtain saturated omega-aminoacids had been contemplated. The methodology set forth in said publications for obtaining this result comprises a plurality of phases including two hydrogenation stages which are successive and clearly distinguished from one another.

The first of said stages consists in the reductive amination of an unsaturated ω-aldehydoacid to the corresponding unsaturated ω-aminoacid, characterized by the fact that the unsaturated ω-aldehydoacid is transformed by means of ammonia and an alkali metal hydroxide in aqueous solution, into the salt of the corresponding unsaturated iminoacid, which latter is hydrogenated in the presence of a catalyst under conditions which lead to the hydrogenation of the imino group. The second of these stages consists in the hydrogenation of the unsaturated ω-aminoacid thus obtained to the corresponding saturated aminoacid, characterized by the fact that the alkali salt of the unsaturated aminoacid is reacted with hydrogen in the presence of a second catalyst, in order to hydrogenate the olenifinc double bonds.

According to this previous methodology the hydrogenation catalyst of the first hydrogenation stage is preferably nickel, in the form of the metal or of salts thereof, pure or supported, or Raney nickel, whereas the second stage hydrogenation catalyst is preferably palladium in supported form. It had not been foreseen, nor was it in fact foreseeable in the light of the previous technical knowledge, that the two distinct hydrogenation stages could be conveniently substituted by a single stage using a single hydrogenation catalyst. Actually, if the catalyst employed for the hydrogenation of the imino groups were used under conditions (temperature above 150° C) such as concurrently to catalyze the hydrogenation of the olefinic double bonds as well, one would obtain, beside the saturated ω-aminoacid, large quantities of undesired by-products, such as e.g. the corresponding secondary aminoacids, which are very harmful to the transformation of the ω-aminoacid to the corresponding polyamide as they would cause a crosslinking of the polyamide and the consequent lack of fusibility of the product. Likewise, if the catalyst for the hydrogenation of the olefinic double bonds (palladium) were concurrently used for the hydrogenation of the imino groups as well, one would equally obtain large amounts of secondary aminoacids as by-products, beside the ω-aminoacids.

SUMMARY OF THE INVENTION

It is now a purpose of the present invention to produce linear saturated omega-aminoacids, corresponding to the general formula

$$H_2N-(CH_2-)_{n+1}COOH \quad (II)$$

wherein "$n$" is a whole number in the range from 4 to 16, and in general from 4 to 10. In view of the substantially identical behaviour of the various compounds, it is held that it is sufficient that examples be given of the production of omega-aminoacids according to the above defined general formula, wherein "$n$" is 6 and 10.

The process according to the present invention is characterized essentially by the fact that the said production is effected through a single stage hydrogenation, starting from unsaturated aldehydoacids comprising from 1 to 3 olefinic double bonds, and corresponding to the general formula (I) hereinbefore set forth, to obtain, with yields above 80%, corresponding saturated aminoacids as defined by the said general formula (II).

According to the invention, an ω-aldehydoacid according to the general formula (I) is transformed into the corresponding iminoacid, and this is subjected to the hydrogenation both of the imino function and of the ethylenic double bond or double bonds, in a single stage and in the presence of an hydrogenation catalyst consisting of a transition metal of one of the first two sub-groups of the VIII group of the elements' periodic system, viz. chosen among Fe, Ru, Os, Co, Rh, and Ir, preferably ruthenium or rhodium.

In practice the iminoacid is obtained as an alkali salt by treatment with ammonia and an alkali metal hydroxide in aqueous solution, according to reaction diagram (III) set forth hereinafter, and is hydrogenated without isolating it, according to reaction (IV). Reactions (III) and (IV) may be carried out in a single stage, by reacting the aldehydoacid concurrently with ammonia, alkali hydroxide and hydrogen in the presence of the catalyst, or the alkali salt of the iminoacid, or a part thereof, may be firstly formed according to reaction (III) and the hydrogenation may be carried out thereafter in a single stage, whereby in any case there is obtained the alkali salt of the desired saturated aminoacid, from which the acid is obtained by treatment with an acid compound, according to known methods (V).

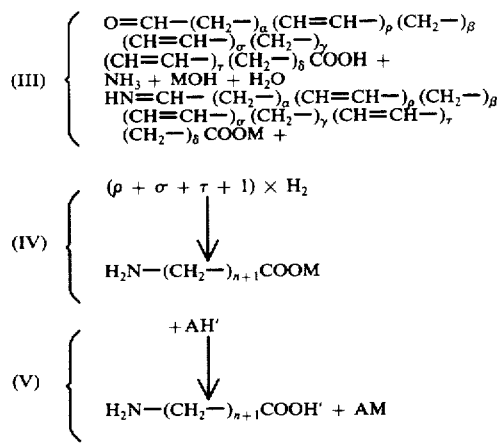

wherein
M = an alkali metal;
H' = an hydrogen atom of an acid compound;
A = the residue of an acid compound;
α, β, γ, σ, τ, ι, τ, n have the meanings specified hereinbefore.

The metal chosen as the hydrogenation catalyst may be used in the metal state or as a compound, pure or preferably supported on a support such as activated charcoal, calcium carbonate, aluminium, silica, or silica-alumina.

The hydrogenation temperature is from 70° to 150° C, preferably from 100° to 140° C.

The aqueous solution of the alkali salt of the iminoacid which forms when aldehydoacid, ammonia and alkali metal hydroxide are mixed, should have an ammonia concentration from 10% to 50% (preferably from 20% to 30%) by weight of $NH_3$ per weight of overall solution, to avoid the formation of secondary products, on the one hand, or a lowering of the solubility of the salt, on the other.

Preferably but not necessarily the conditions are also observed that
the hydrogen pressure for the hydrogenation is from 2 to 60 atmospheres;
the duration of the hydrogenation is from 1 to 8 hours.

One of the main advantages obtained through the use of the process according to the invention, is that the whole sequence of all the reactions illustrated in the general reaction diagrams (III), (IV) and (V) occurs with yields of saturated ω-aminoacid, referred to the initial ω-aldehydoacid, of at least 80% of the theoretical value.

Other important advantages, with respect to the process disclosed in the above mentioned patent publications, are the following:
1. Yield of at least 80% of saturated ω-aminoacid, while the previously known (single stage) techniques did not go over 70%. Therefore the losses of the starting ω-aldehydoacid are limited. Said yields are close to those which are attained by the previously known two stage process.
2. The high yield facilitates the successive purification process, inasmuch as the by-products which are present are very few.
3. Simplicity of the process, which is carried out in a single stage, whereas the previously known methods involved two hydrogenation autoclaves and the filtration of the catalyst between the first and the second stage. Therefore investment and operation costs are lower.

DESCRIPTION OF THE PREFERRED EMBODIMENTS

A number of preferred but not exclusive embodiments will be set forth hereinafter, together with a number of comparative examples, for the purpose of better demonstrating the progress afforded by the invention to the state of the art.

EXAMPLE 1

50 g. of ruthenium at 5% on charcoal (having a moisture content of 50%), 220 g. of a 32% by weight aqueous ammonia and hydrogen in the amount required to reach an overall pressure of 20 atm., are charged into a stainless steel autoclave having a volume of 2.7 liters, provided with a fast stirrer, a temperature control system and a dosing volumetric pump. Stirring is begun and concurrently the autoclave is heated up to 130° C. At this temperature the pressure becomes stabilized at 30 atmospheres.

In 16'there are fed into the autoclave, through the volumetric pump, 787 g. of an aqueous ammonia containing solution having the following composition: 92% 11-formyl-4,8-undecadienoic acid: 150.5 g.; aqueous (32% by weight) ammonia: 525 g.; aqueous (24.9% by weight) sodium hydroxide: 101.8 g.; water: 10 g.

While the imine solution is being fed into the autoclave, the temperature is maintained at 130°-132° C; the pressure is maintained at 30 atmospheres by feeding hydrogen. At the end of the pumping of the imine solution, the reaction is continued for another 140'and then the solution contained in the autoclave is discharged through a filter and is concentrated so as to evaporate all the excess ammonia.

The aqueous solution of the sodium salt of the aminoacid is purified by extraction with toluene. From the toluene solution small amounts of dodecamethylene-diamine are obtained. From the aqueous solution, by treatment with carbon dioxide at room pressure and at a temperature of 98° C, 12-amminododecanoic acid is obtained as a crystalline precipitate. The yield is 116.5 g. (82.5% of theory referred to the aldehyde groups of the initial formylundecadienoic acid).

EXAMPLES 2 and 3 (comparative)

In order to illustrate the advantages attained through the use of the catalysts herein described and claimed, in a comparison with catalysts consisting of other transition metals of the eighth group of the elements' periodic system, the results obtained with these latter in the amino-hydrogenation reaction of 11-formyl-4,8-undecanoic acid are set forth hereinafter. The hydrogenation conditions are the same as used in Example 1.

| Example N° | Catalyst | Yield of 12-aminododecanoic acid % |
|---|---|---|
| 2 | 5% Pt on charcoal | 20.5 |
| 3 | 5% Pd on charcoal | 49.8 |

The yield is referred to the aldehyde groups of the initial 11-formyl-4,8-undecadienoic acid.

EXAMPLE 4 (comparative)

With the same purposes as in Examples 2 and 3, a comparison is made of the behaviour of finely divided nickel as a catalyst for the hydrogenation both of the imino groups and of the olefinic double bonds. The ydrogenation of the first is effected under the conditions described in Example 1, whereas for the hydrogenation of the olefinic double bonds the use of a temperature of 170° C is required. The starting material and the other conditions are the same as used in Example 1.

After purification, 12-aminoundecanoic acid is obtained with a yield of 60% referred to the aldehyde groups of the starting material.

EXAMPLE 5

Example 1 is repeated using 7-formyl-4-heptenoic acid (148 g.) as a starting material to be subjected to the amino-hydrogenation. The catalyst employed is ruthenium metal (55 g. at 5%, supported on charcoal) which is loaded into the autoclave as described in Example 1. The reaction is carried out at 135° C and at 40 atmospheres and the absorption of hydrogen lasts 180' after the end of the pumping of the ammonia containing solution of the unsaturated aldehydoacid. At the end of the reaction, after filtering the catalyst, the excess ammonia is evaporated, the solution is concentrated to a small volume and it is acidified with a weak acid. Upon the addition of alcohol, 8-amino-octanoic acid, m.p. 188°-190° C, is separated (yield 85%).

EXAMPLE 6

Example 1 is repeated using rhodium metal as the catalyst. 20 g. of 5% rhodium (supported on charcoal) and 150 g. of concentrated ammonia are charged into the autoclave having a volume of 2.7 liters described in Example 1. The temperature of the autoclave is brought to 13° C, the pressure is brought to 30 atmospheres by means of hydrogen, and an ammonia containing aqueous solution of 11-formyl-4,8-undecadienoic acid in the amount and with the composition set forth in Example 1 is pumped into the autoclave. After the introduction of the aldehydoacid has ended, the temperature is brought to 135°-138° C and the pressure to 45 atmospheres. The absorption of hydrogen continues for 300 more minutes, then the pressure is discharged from the autoclave, the catalyst is filtered and the 12-aminododecanoic acid is separated from the solution as described in Example 1. (Yield 120 g. = 84.5% referred to the aldehyde groups of the formylundecanoic acid employed).

The examples which have been described have only an illustrative value, as the invention may be carried into practice in many other ways, without departing from the scope of this patent.

We claim:

1. Process for the preparation of saturated omega-aminoacids having the general formula $H_2N-(CH-)_{n+1}COOH$ wherein "$n$" is a whole number in the range from 4 to 16, from linear unsaturated omega-aldehydoacids comprising from 1 to 3 olefinic double bonds, and having the general formula

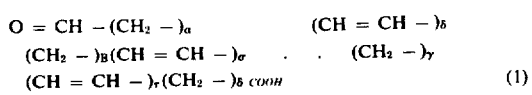

wherein $\alpha, \beta, \gamma, \delta$ = whole numbers, equal or different from one another, chosen among 0,1,2 and 3;

$\rho, \sigma, \tau$ = whole numbers, equal or different from one another, chosen among 0 and 1;

and wherein the sum $\rho + \tau + \tau = 1,2$ or 3;

and wherein the sum $\alpha + \beta + \gamma + \delta + \rho + \sigma + \tau = n$, characterized by the fact that an $\omega$-aldehydoacid according to general formula (I) as set forth in the description, is reacted with ammonia and an alkali metal hydroxide in aqueous solution according to general reaction (III), whereby the alkali salt of the corresponding iminoacid is obtained, that this latter is reacted with hydrogen in the presence of an hydrogenation catalyst giving rise to general reaction (IV) and that the saturated $\omega$-aminoacid is then obtained from its alkali salt by treatment with an acid compound according to reaction (V), all as follows:

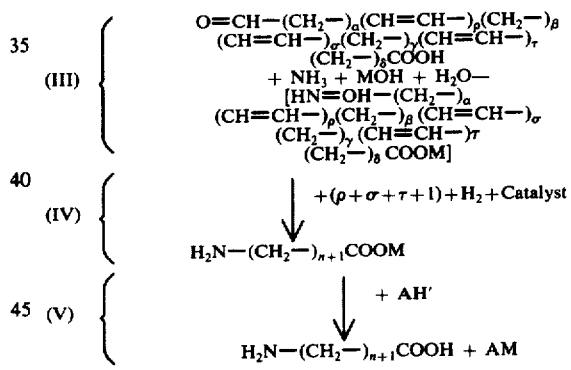

wherein $M$ = an alkali metal;

$H'$ = an hydrogen atom of an acid compound;

$A$ = residue of an acid compound;

$\alpha, \beta, \gamma, \delta, \rho, \sigma, \tau, n$, have the meaning set forth hereinbefore; provided that:

the hydrogenation catalyst is a metal chosen from the group consisting of Fe, Ru, Os, Rh, V and Ir;

the hydrogenation temperature is from 70° to 140° C;

the aqueous solution of the alkali salt of the iminoacid which forms when acid aldehyde, ammonia and metal alkali hydroxide are mixed, has an ammonia concentration from 10% to 50%, expressed as weight of $NH_3$ per weight of overall solution.

2. Process according to claim 1, characterized in that reactions (III) and (IV) are carried out in a single operative stage.

3. Process according to claim 1, characterized in that reactions (III) and (IV) are carried out in successive time periods.

4. Process for the preparation of saturated omega-aminoacids from olefinically unsaturated omega-aldehydoacids, which comprises reacting the aldehydoacid with ammonia to form the corresponding iminoacid and the hydrogenating of the imine function and the ethylenic double bond or double bonds of said imino-acid whereby the corresponding saturated omega-amino acid is obtained, said hydrogenating of the imine function and the double bond or double bonds being carried out in a single reaction stage by treatment with hydrogen in the presence of a catalyst selected from the group consisting of ruthenum and rhodium.

5. Process according to claim 1 wherein the hydrogenation catalyst is employed in the metal state.

6. Process according to claim 1, wherein the hydrogenation catalyst is employed as a compound.

7. Process according to claim 1, wherein the hydrogenation catalyst is supported on a support consisting essentially of a substance chosen from among activated charcoal, alumina, silica and silica-alumina.

8. Process according to claim 4, wherein the omega-aldehydoacid is reacted with ammonia in the presence of an alkali metal hydroxide in aqueous solution and the resulting alkali metal salt of the corresponding iminoacid is hydrogenated without isolating said metal salt, whereby the alkali salt of the corresponding saturated omega-aminoacid is obtained.

9. Process according to claim 4, wherein the preparation of the alkali salt of the imino-acid and the hydrogenation of said salt are carried out in a single reaction stage.

10. Process according to claim 9, wherein the preparation of the alkali salt of the imino-acid and the hydrogenation of said salt are carried out at least in part in successive reaction stages.

11. Process according to claim 8, wherein the alkali metal salt of the saturated omega-amino acid is treated with an acid to obtain the free aminoacid.

12. Process according to claim 4, wherein the hydrogenation is carried out at a temperature from 70° to 150° C.

13. Process according to claim 8, wherein the alkali salt of the iminoacid is maintained in solution in water at an ammonia concentration from 10 to 50%, expressed as weight of $NH_3$ per weight of overall solution.

14. Process according to claim 4, wherein the hydrogenation catalyst is employed in the metal state.

15. Process according to claim 4, wherein the hydrogenation catalyst is employed as a salt thereof.

16. Process according to claim 4, wherein the hydrogenation catalyst is supported on a support consisting of a substance or a compound chosen among activated charcoal, alumina, silica, and silica-alumina.

17. Process according to claim 4, wherein the hydrogenation temperature is from 100° to 140° C.

18. Process according to claim 1, wherein the ammonia concentration of the solution of the alkali salt of the iminoacid is from 20 to 30% by weight of $NH_3$.

19. Process according to claim 4, wherein the hydrogenation is carried out at a hydrogen pressure from 2 to 60 atmospheres.

20. Process according to claim 4, wherein the duration of the hydrogenation is comprised between 1 to 8 hours.

* * * * *